United States Patent [19]

Nussbaumer

[11] Patent Number: 4,692,160

[45] Date of Patent: Sep. 8, 1987

[54] URINE COLLECTOR FOR INCONTINENT WOMEN HAVING ZIG-ZAG WALLS

[76] Inventor: Max Nussbaumer, Scheibenstrasse 13, CH-3014 Bern CH, Switzerland

[21] Appl. No.: 818,805

[22] PCT Filed: May 14, 1985

[86] PCT No.: PCT/CH85/00081

§ 371 Date: Jan. 14, 1986

§ 102(e) Date: Jan. 14, 1986

[87] PCT Pub. No.: WO85/05264

PCT Pub. Date: Dec. 5, 1985

[30] Foreign Application Priority Data

May 15, 1984 [CH] Switzerland .......................... 2375/84

[51] Int. Cl.$^4$ ................................................. A61F 5/44
[52] U.S. Cl. ..................................................... 604/331
[58] Field of Search ................................. 604/327–331; 4/144.1–144.4

[56] References Cited

U.S. PATENT DOCUMENTS 3,194,238 7/1965 Breece ............................... 604/329
3,349,768 10/1967 Keane ................................ 604/329

FOREIGN PATENT DOCUMENTS 1766795 7/1968 Fed. Rep. of Germany .
1236346 6/1960 France ................................. 4/144.3
610523 6/1978 U.S.S.R. .............................. 604/327

Primary Examiner—C. Fred Rosenbaum
Assistant Examiner—J. L. Kruter
Attorney, Agent, or Firm—Sherman and Shalloway

[57] ABSTRACT

In a part (2) comprised of a slightly elastic material, a collector structure (11) is arranged above a collecting cavity (19) provided with an outlet (7). The collector structure (11) is comprised of two side pieces (11a, 11b) in the form of zigzag-shaped prominences. The structure delimits a wet zone (22), while a moist zone (23) is delimited by the lateral regions (18a, 18b) of the border (18) together with a rear bead (17) and a front bead (15). The collector structure (11) is placed between the labia minora and labia majora of the woman, while the elements delimiting the moist zone come to lie outside the labia majora. The inventive urine collector enables incontinent women to freely move about without risk of their garments being contacted with urine.

9 Claims, 26 Drawing Figures

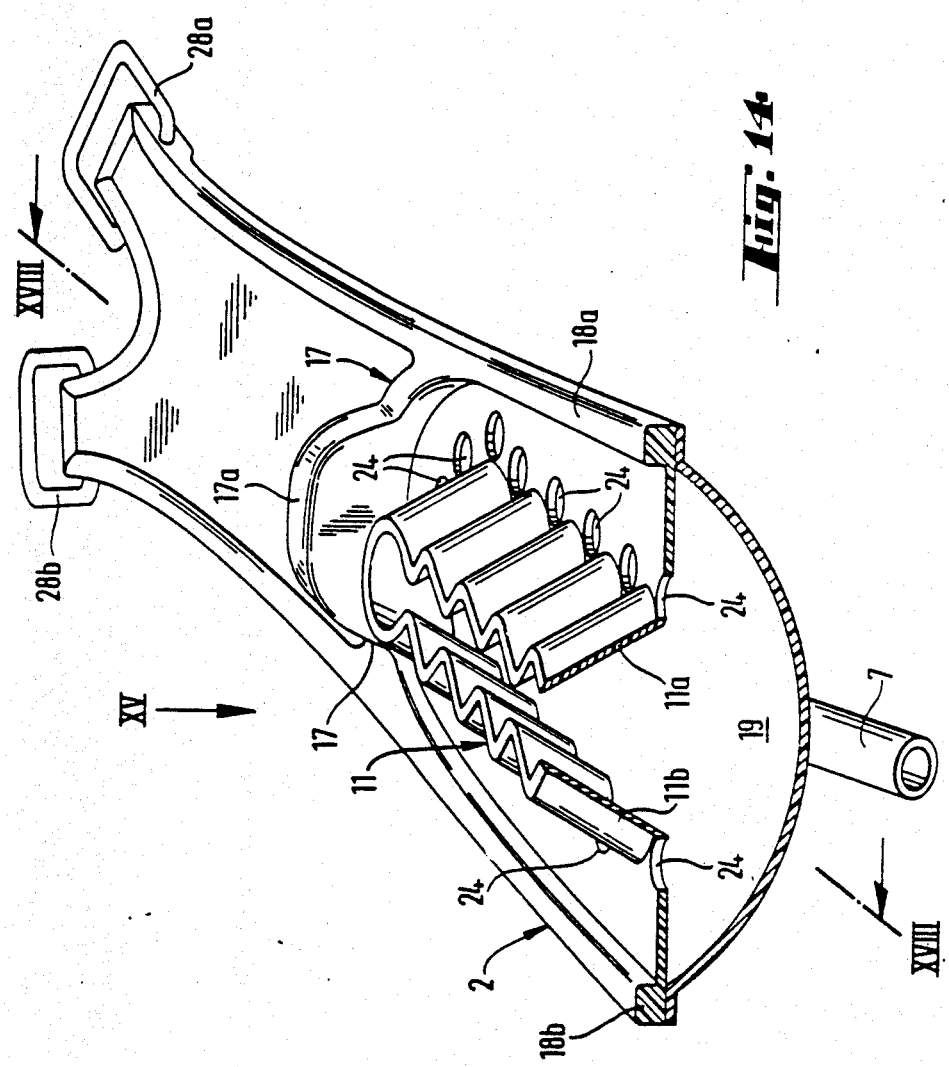

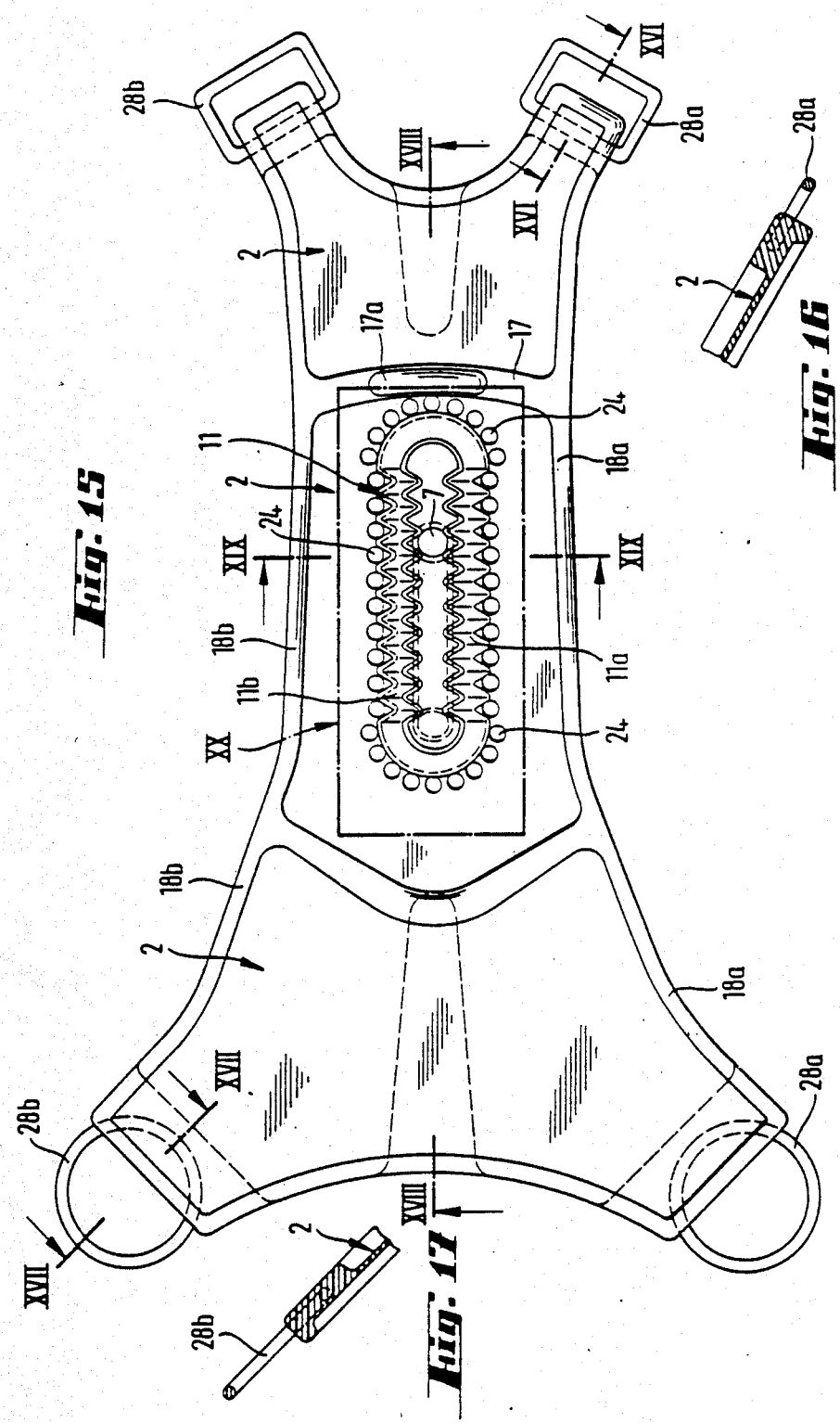

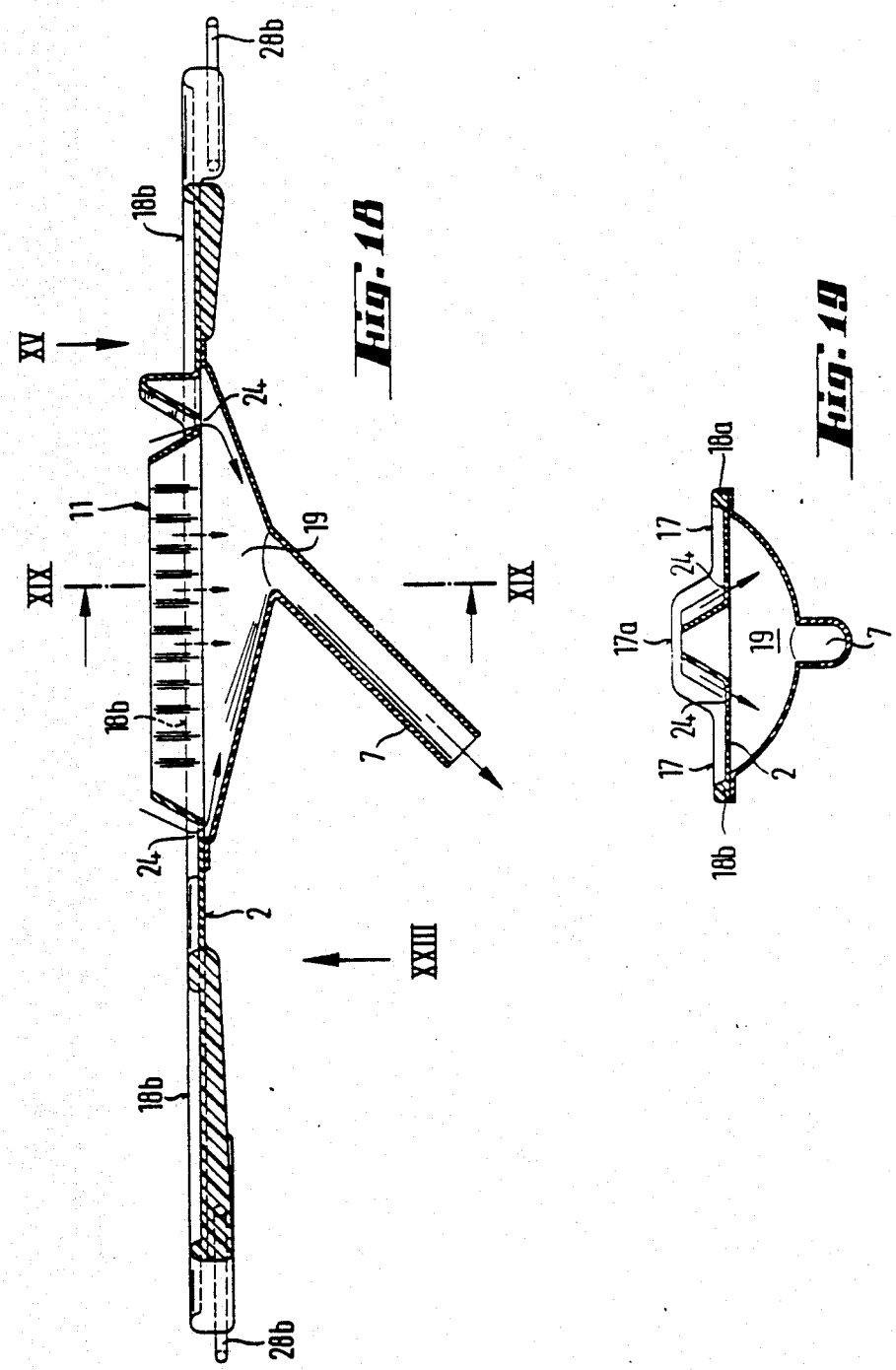

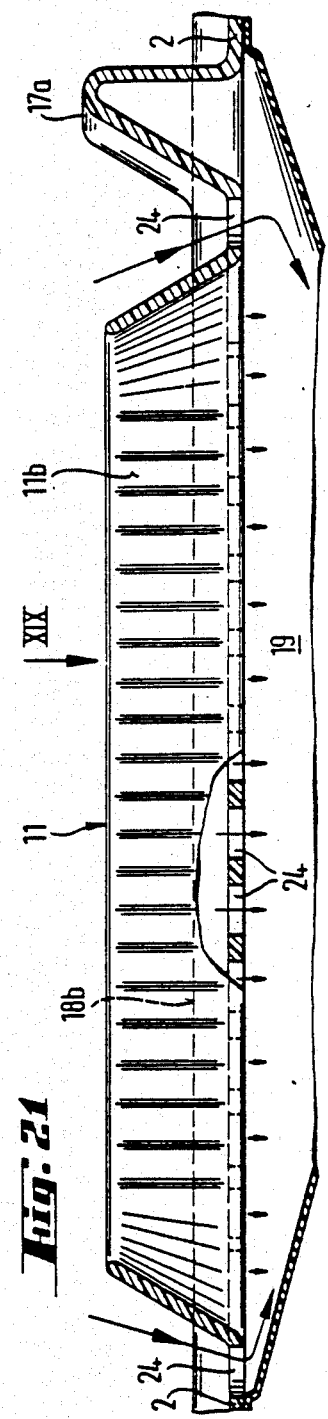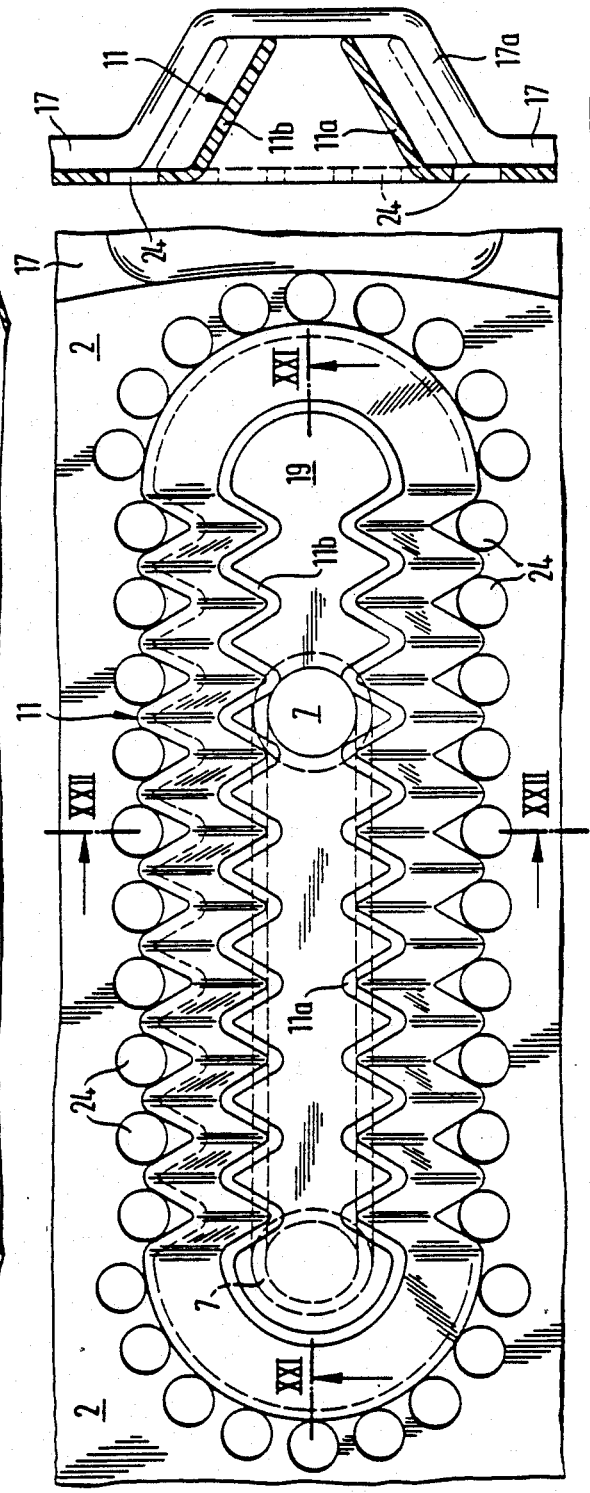

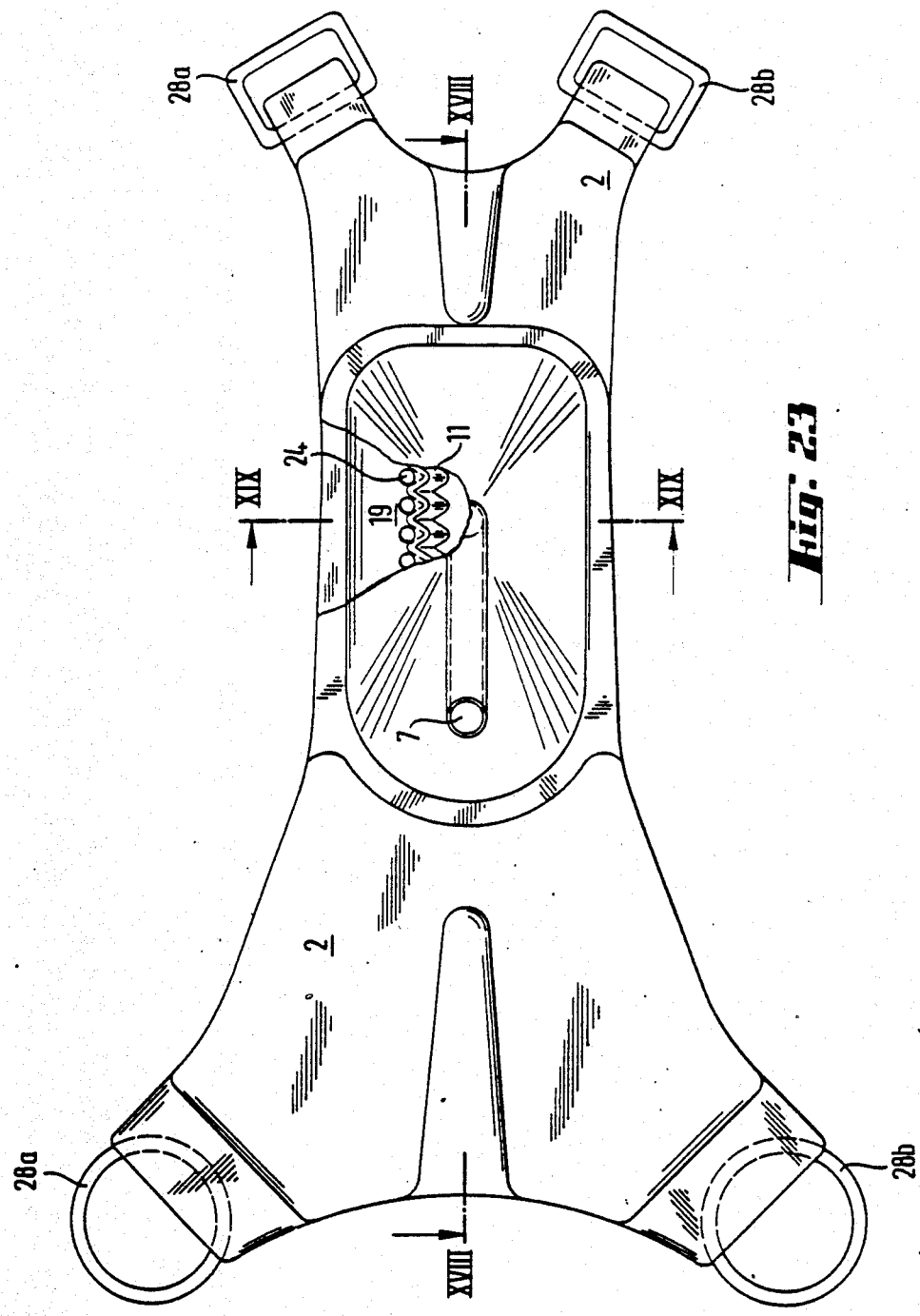

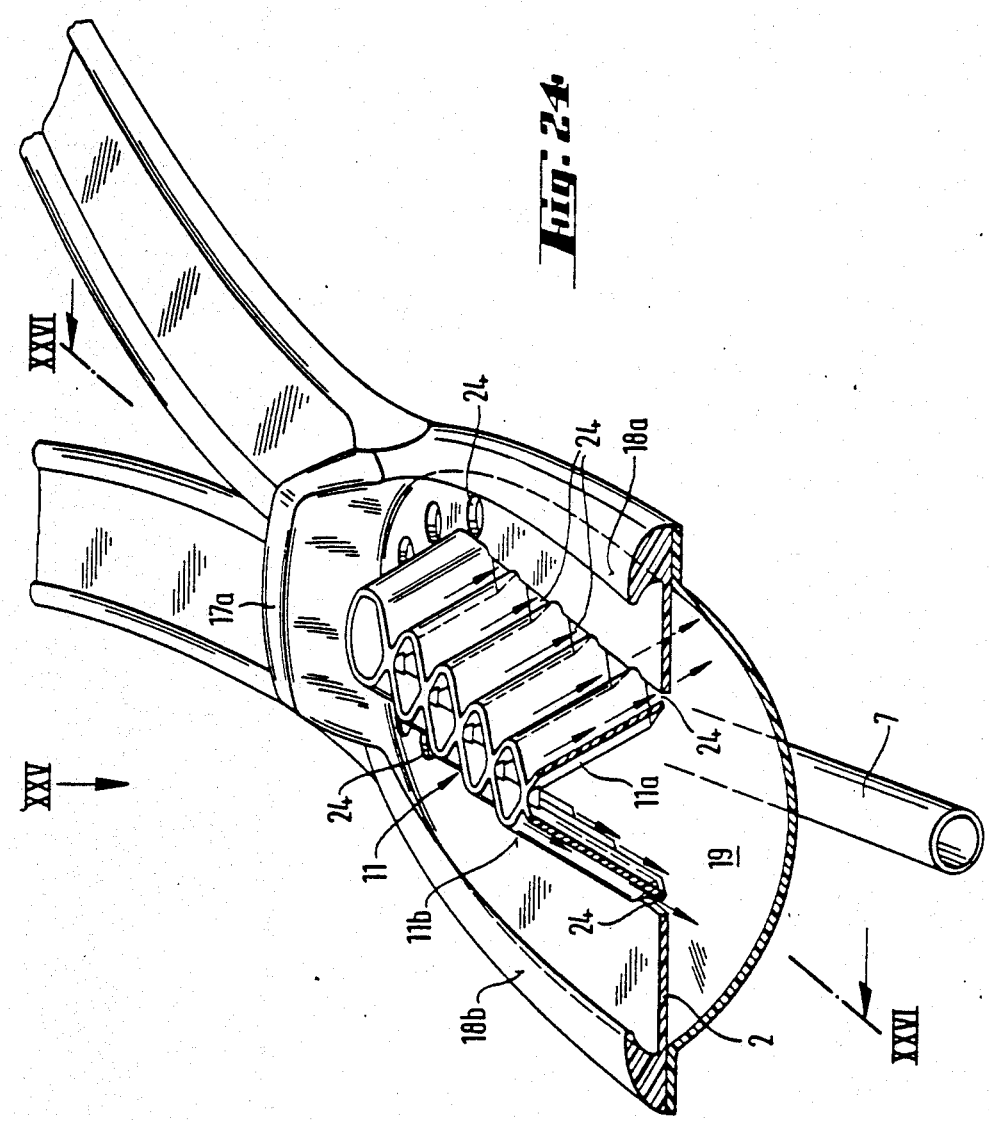

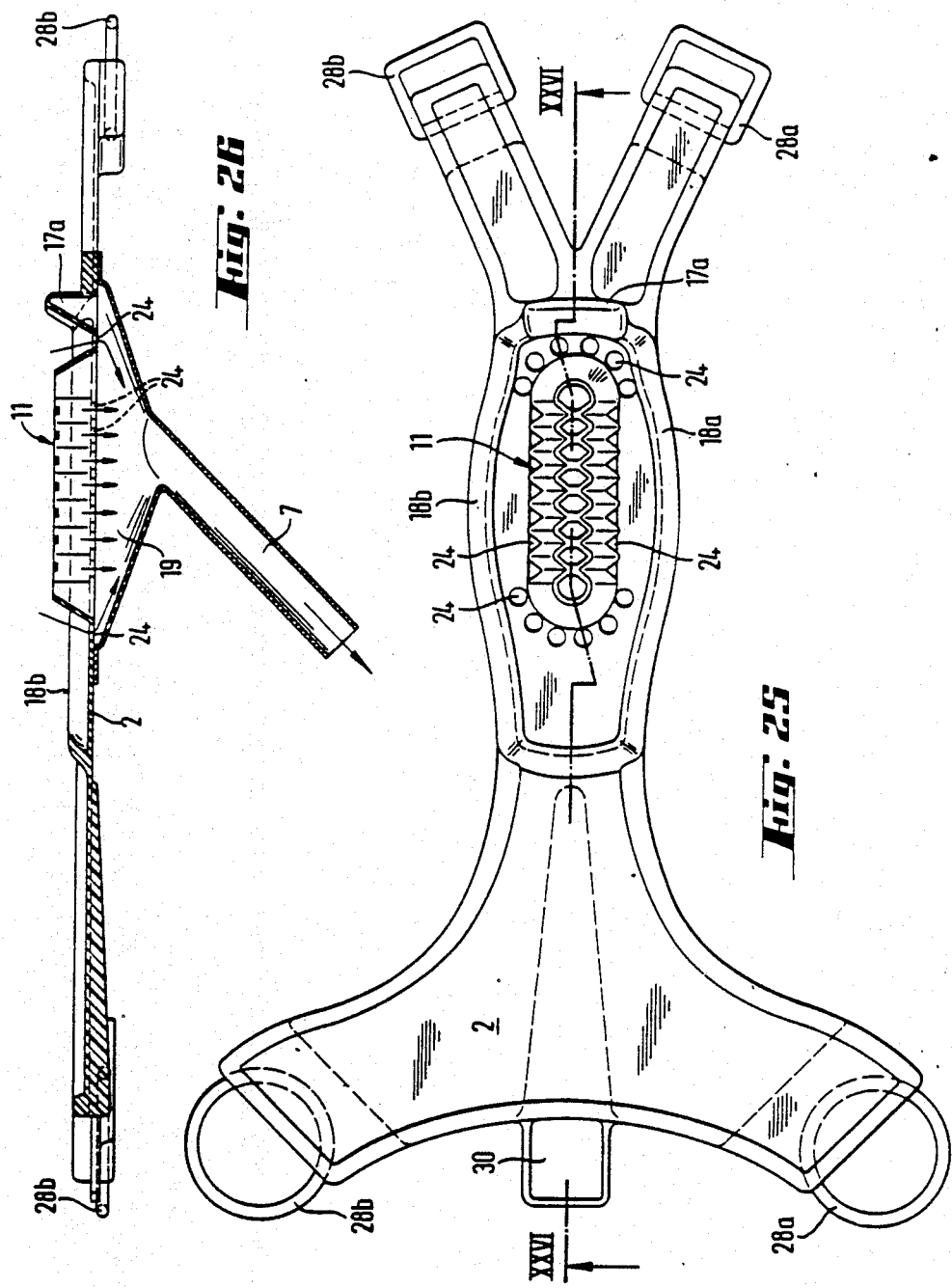

URINE COLLECTOR FOR INCONTINENT WOMEN HAVING ZIG-ZAG WALLS

The invention relates to a urine collector for incontinent women.

Background of the Invention

The problem of collecting urine coming uncontrolled from the bladder and urethra is quite different and much more complex for incontinent women than for men, since for the latter a collecting bag may be simply inverted over the penis.

Because in women the urethra ends between the inner labia (labia minora) where it is not possible to readily attach a collecting bag or other collector, incontinent women have heretofore had to resort to diapers or similar aids. Known collectors, e.g. according to Jap. Pat. No. 1,062,936 or similar contrivances, have proven impractical to manage and/or uncomfortable to wear, as well as being frequently leaky. Further, many find it objectionable to carry to wear an anal stimulator (according to still another known proposal) to employ such to stimulate, among other things, the bladder-closing muscle, so as to overcome the incontinence.

Accordingly, the underlying problem of the invention is to devise a urine collector for incontinent women which is easy to manipulate, is minimally irritating when worn for extended periods, and is maximally secure (i.e., nonleaking) in all situations.

According to the invention this problem is solved by a urine collector as recited in the accompanying claims.

Advantageous variants of embodiments of an inventive urine collector will now be described in detail, with reference to the drawings.

BRIEF DESCRIPTION OF THE DRAWINGS

FIG. 14 is a perspective partial cross sectional view of a third variant embodiment of an inventive urine collector;

FIG. 15 is a plan view of the urine collector of FIG. 14;

FIGS. 16 and 17 are longitudinal cross sectional views of details of the embodiment of FIG. 14;

FIG. 18 is a longitudinal cross sectional view of the urine collector of FIG. 15, along the line XVIII—XVIII;

FIG. 19 respectively is a cross sectional view of the same urine collector, along lines XIX—XIX of FIGS. 18 and 21;

FIGS. 20, 21 and 22 are enlarged views of details of FIGS. 15, 18, and 19;

FIG. 23 is a bottom view of the variant embodiment of FIG. 14, with a part of the collecting space partially broken away;

FIG. 24 is a perspective, partial cross sectional view of a fourth variant embodiment of an inventive urine collector;

FIG. 25 is a plan view of the embodiment of FIG. 24; and

FIG. 26 is a longitudinal cross sectional view of the urine collector of FIG. 25, along line XXVI—XXVI.

Description of The Preferred Embodiment

Figure 1:
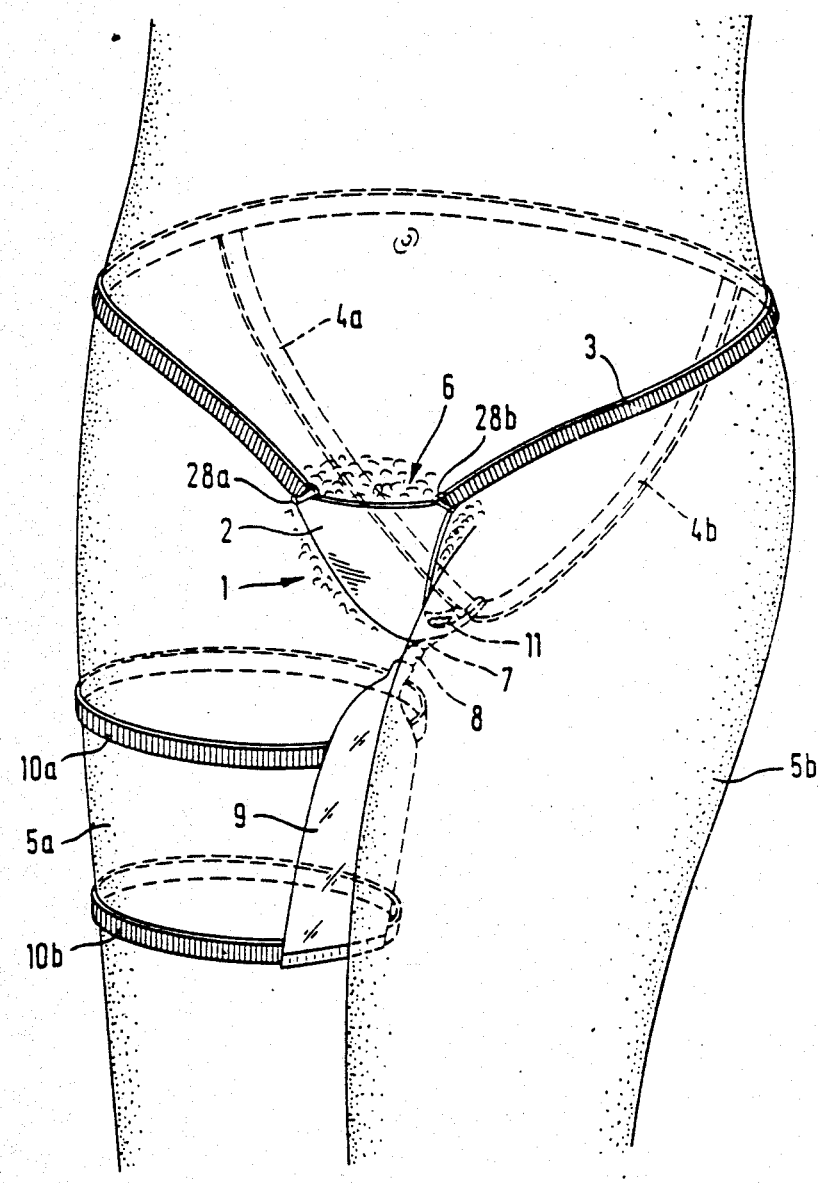
FIG. 1 is a front view of an inventive urine collector with basic accessories, being worn by a woman.

In FIG. 1 the inventive urine collector is shown in its operative position worn abdominally by a woman. Parts of the collector are shown only with dotted lines, being hidden by one of the woman's thighs and her lower torso. The following general parts of the inventive urine collector, along with the associated accessory means, are shown in this FIG. 1: The urine collector, designated in general 1; and the part 2 of the collector 1, which part 2 is held in the correct position by a waist belt 3 and a two-part auxiliary belt (4a, 4b), said correct position being between the thighs (5a, 5b) and in the perineal region 6 of the woman wearing the urine collector. An outlet 7 can be seen on part 2, which outlet opens out via an intermediate piece 8 into a known collecting bag 9 with leg straps 10a and 10b. A collector structure 11 disposed on part 2 is shown only symbolically in FIG. 1. It is seen from FIG. 1 that the inventive urine collector 1 is worn similarly to a bikini bathing suit bottom, wherewith the correct supporting position of the waist belt 3 and the auxiliary belt (4a, 4b) basically ensures proper positioning of the part 2 which part includes the collector structure 11.

Figure 2:
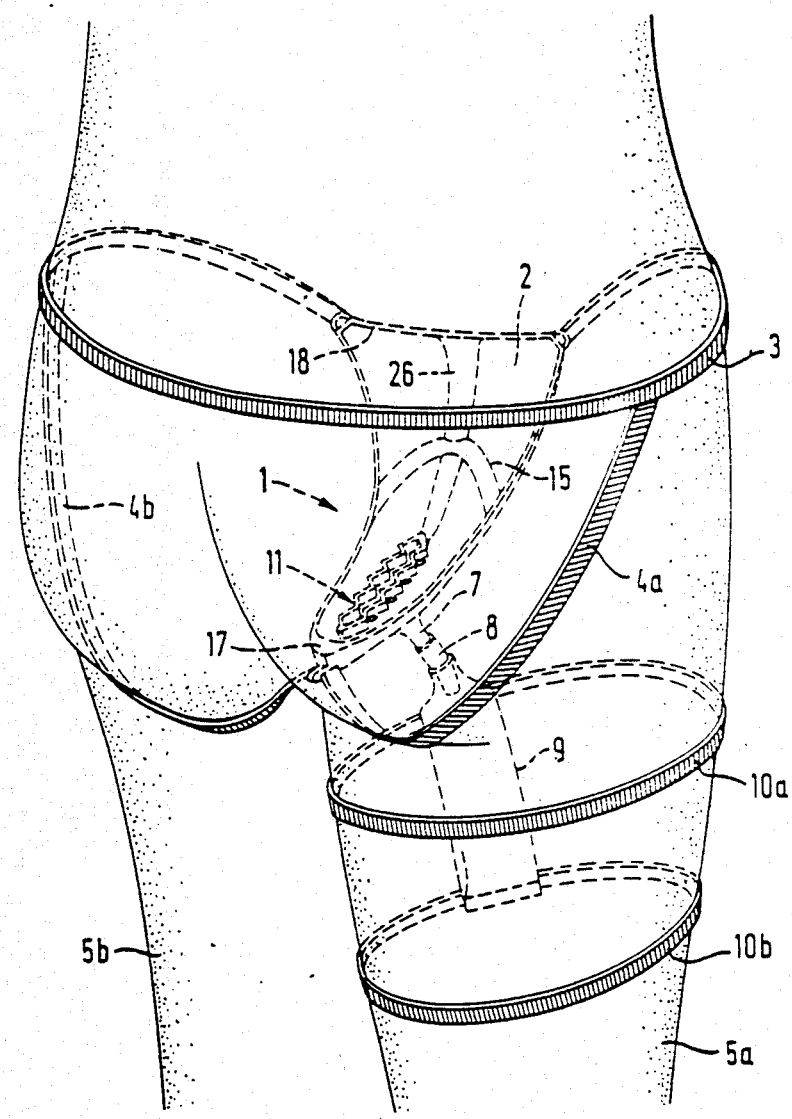
FIG. 2 is a view of the same, from behind and at an angle.

FIG. 2 shows the urine collector 1, along with all of the accessory means illustrated in FIG. 1, from the back side of the woman wearing said collector. Most of the urine collector and the accessory means are necessarily shown in dotted lines.

Figure 3:
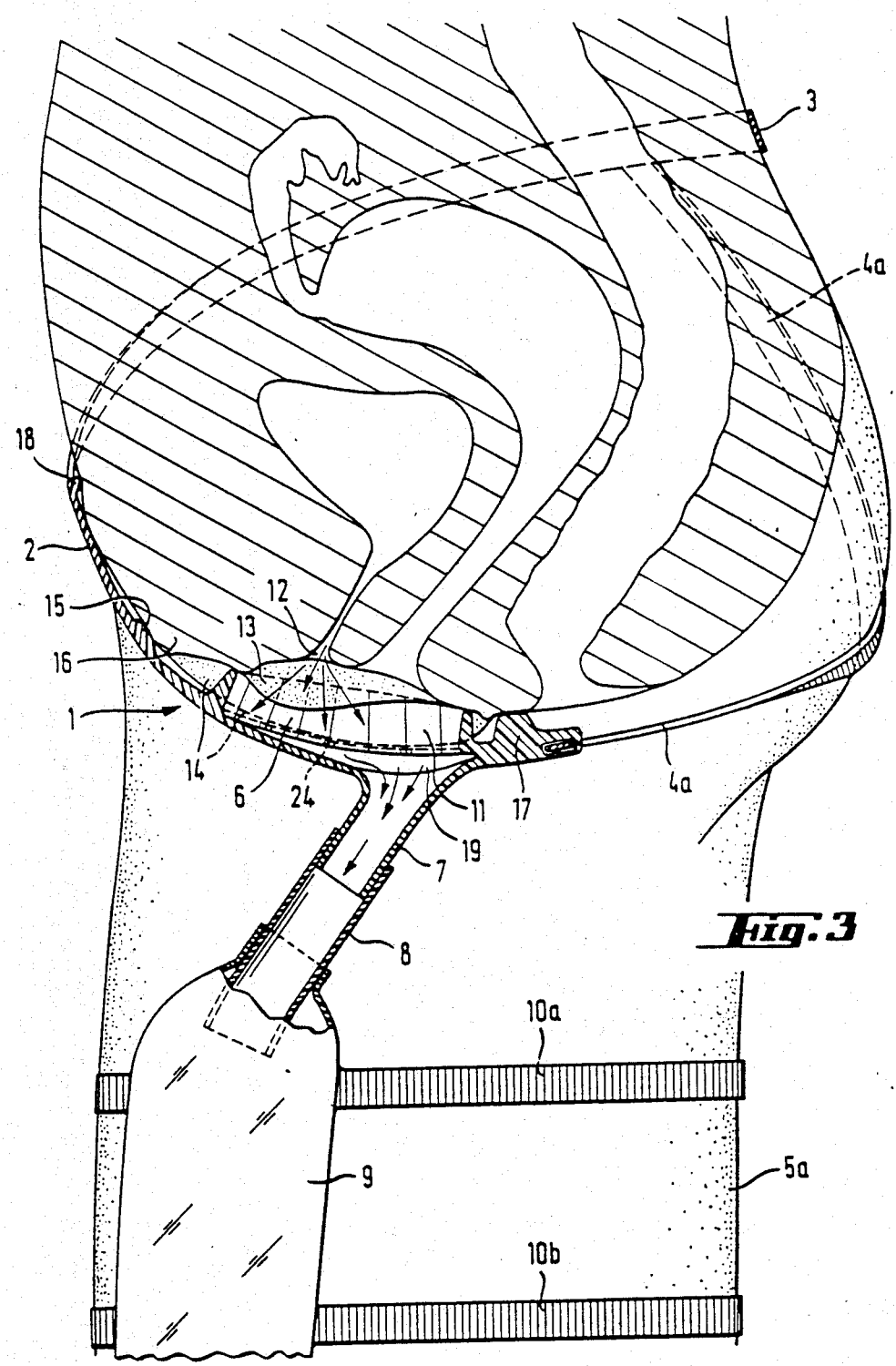
FIG. 3 is a longitudinal cross sectional view through the lower torso of a woman wearing the urine collector, of FIG. 1 which collector is also shown in cross section.

FIG. 3 shows, in longitudinal cross section, how the inventive urine collector 1 rests in the crotch of the woman. The position of the collector structure 11 with respect to the urethral opening 12 and the labia minora 13 and labia majora 14 is not illustrated clearly. However, it can be seen clearly here how a front bead or the like 15 against the pelvic bone 16 seals the urine collector 1 against forward leakage, and a rear bead or the like 17 provides a seal against rearward leakage. These results are achieved in addition to the sealing provided by the collector structure 11 in cooperation with the labia 13 and 14. The border 18 which runs around part 2 provides additional sealing.

It is recommended that the bag used not be the simple bag 9 illustrated but a bag with:

A check valve to prevent urine which reaches the bag 9 from possibly flowing back into the urine collector 1 as a consequence of some posture or position assumed by the woman; and An outlet spout, in order to enable the bag 9 to be emptied without removing said bag.

It is seen from FIG. 3 that the inventive urine collector 1 is kept as small as possible, and covers only the absolutely necessary pubic region 6.

Figure 4:
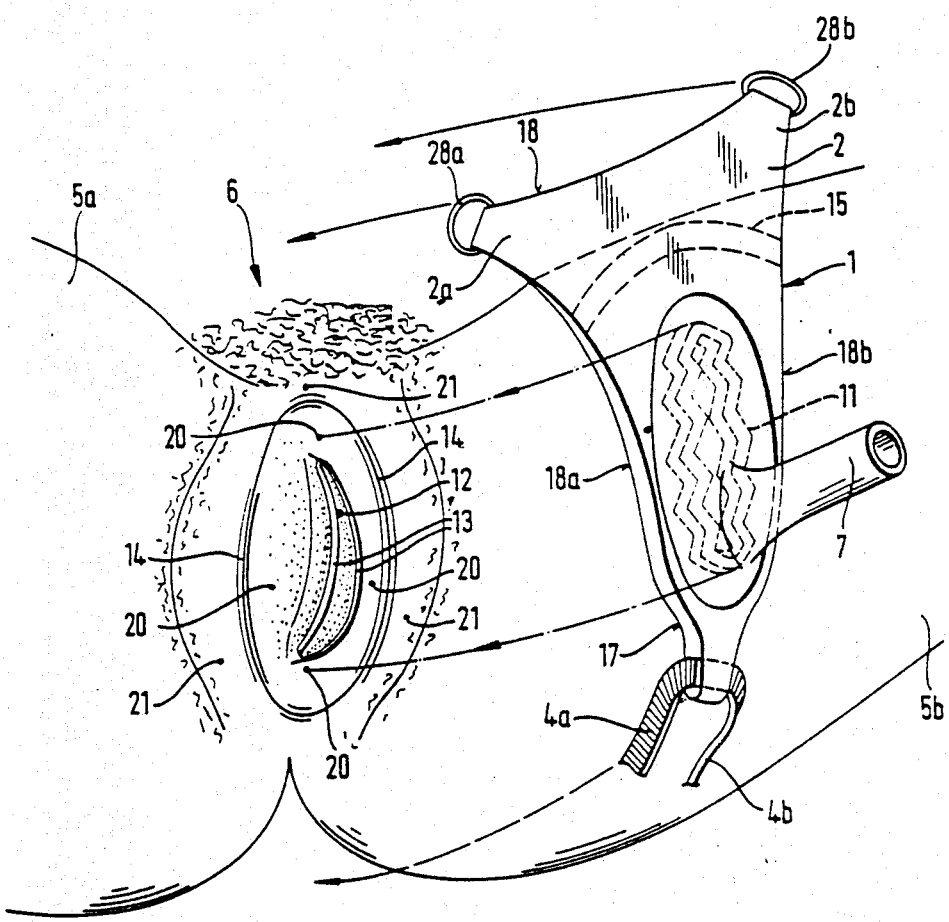
FIG. 4 is a perspective view of a woman's perineal region, with urine collector which is to be applied, which collector is also shown in a perspective view.

FIG. 4 is a perspective exploded view showing where the individual parts of the urine collector 1 are placed on the lower abdomen and the perineal region 6 of the woman. Shown schematically is the disposition of the labia minora 13, between which the urethra opens out at 12 and above which the labia majora 14 are disposed, which labia majora in the normal case are open but (not as shown here) lie over the labia minora.

Figure 5:
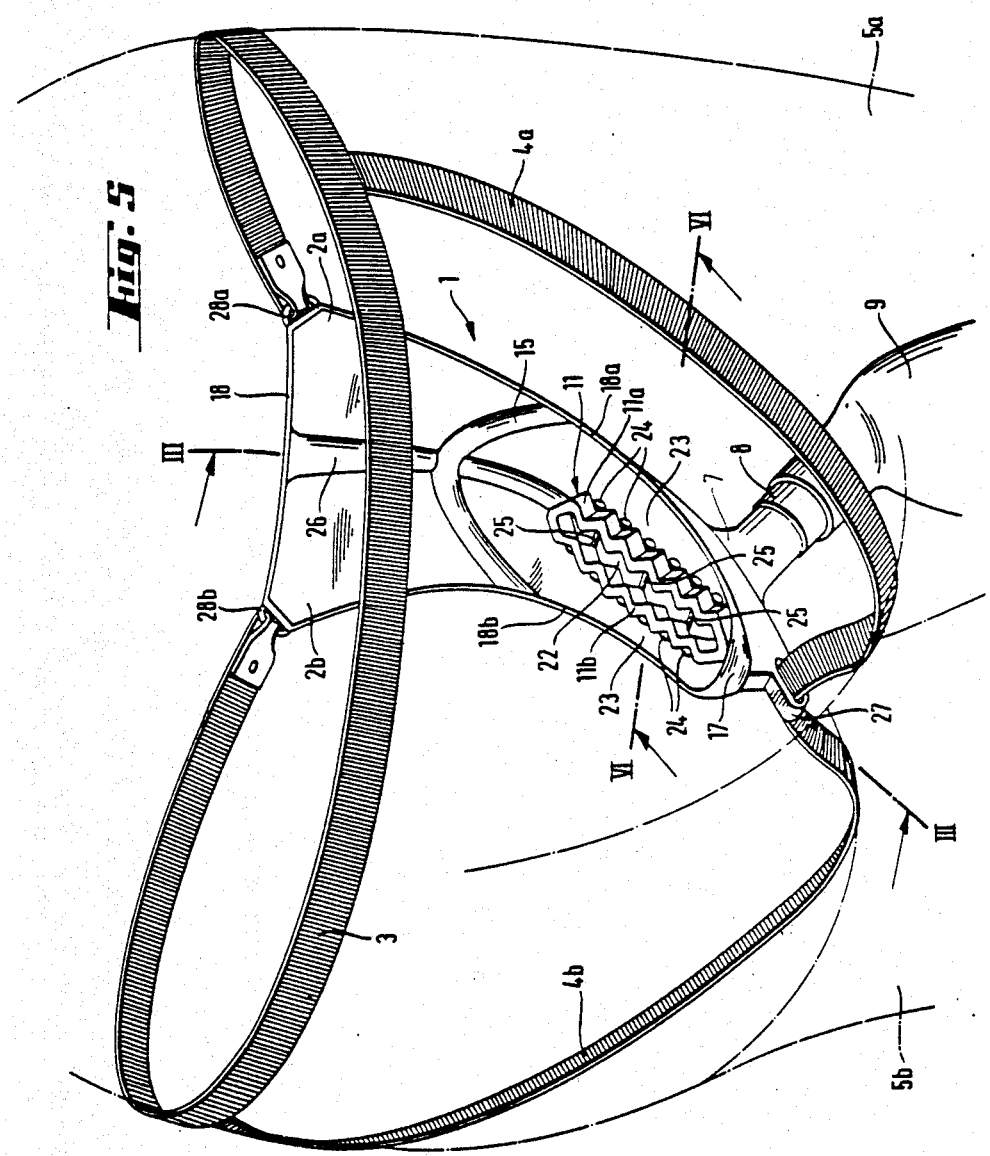
FIG. 5 is a perspective view, from behind, of a urine collector according to FIG. 1 in position as worn abdominally.

As a rule, a woman not having exceedingly small labia minora 13 will wear the here-illustrated first variant embodiment of the urine collector 1 such that the collector structure 11 (the details of which structure will be described infra) is placed between the labia minora 13 and labia majora 14 in the application region 20 (see also FIG. 6). In this way, an inner zone is delimited beyond which under normal conditions urine exiting from the meatus 12 cannot penetrate, since the collector structure 11 guides the urine flowing past the labia minora 13 into the collecting cavity 19 (FIG. 3), and the labia 13 and 14 are pressed tightly against the collector structure 11. This wet zone 22 (FIG. 5) is kept sealed such that urine does not flow out of it in any ordinary position assumed by the woman or during any unexaggerated movement. Even if, contrary to expectation, this should occur, the lateral regions 18a and 18b of the border (which regions in the forward part undergo a transition to the front bead 17) serve as a secondary, outer seal in the application region 21 outside of the labia majora 14, to prevent leakage beyond the pubic region. Any urine which may penetrate to this outer zone, denominated the moist zone 23, is also passed along the collector structure 11 and into the collecting cavity 19 (FIG. 3) vis drainage holes 24 (FIG. 5). The urine flows from the collecting cavity and out of the urine collector 1 through the outlet 7, and into a bag 9 (FIG. 3), preferably via an intermediate piece 8.

FIG. 5 is a view from below of the inventive urine collector 1 in the position as worn, wherewith the lower torso of the woman is shown only symbolically and the details of the perineal region covered by the urine collector 1 and interacting with said collector are omitted. One can see well in FIG. 5 the shell-like configuration of the urine collector 1 on the lower torso. Also well illustrated are the wet zone 22 in the collector structure 11, and the moist zone 23 which is bounded by the lateral regions 18a and 18b of the border 18 and further by the front bead 15 and the rear bead 17. FIG. 5 also shows clearly the spacing members 25 between the two side pieces 11a and 11b of the collector structure 11. The function of the spacing members 25 is to prevent external forces from the labia majora 14 and/or the thighs 5a and 5b from pressing together the two side pieces 11a and 11b such that the urine exiting from the urethra can no longer be guided between the said side pieces 11a and 11b.

Figure 6:
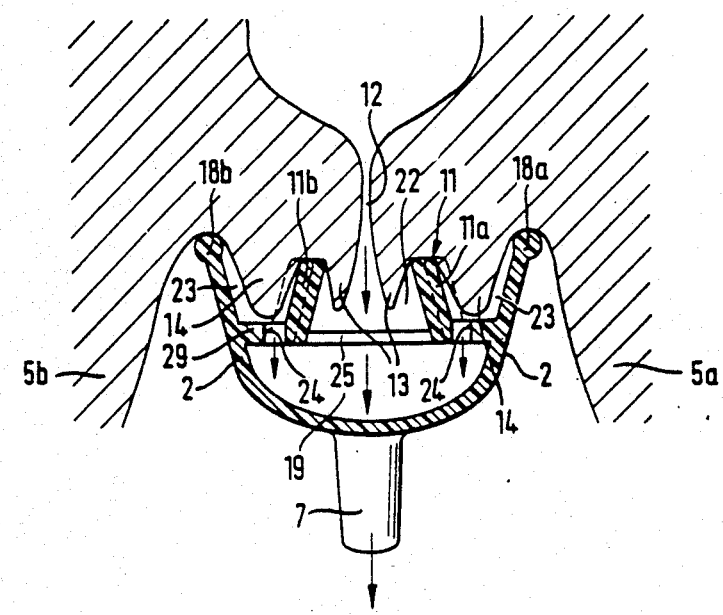
FIG. 6 is a cross sectional view of a first variant embodiment of an inventive urine collector, which collector is being worn.

FIG. 6 shows a urine collector 1 (first variant embodiment) in the position in which worn, in a cross sectional view in the region of the meatus 12. The part 2 may be seen which includes the collector structure 11 the two side pieces 11a and 11b of which are held apart by the spacing members 25. The labia minora 13 as is the usual case are within the collector structure 11, while the labia majora 14 are positioned between the collector structure 11 and the outer part 2 which is reinforced by the lateral regions 18a and 18b of the border 18. The wet zone 22 and the moist zone 23 are clearly separated from each other by the seal produced in the application region 20 (FIG. 4). The urine exiting the urethra can flow unimpeded all along the spacing members 25, along the inner wall of the collector structure 11 and into the collecting cavity 19, and from there through the outlet 7. Urine which reaches the moist zone 23 (due to the woman's unfavorable movements or positions or due to careless application of the urine collector 1) may also be passed into the collecting cavity 19 via the drainage holes 20, and it can flow out from said cavity unimpeded.

Figure 7:
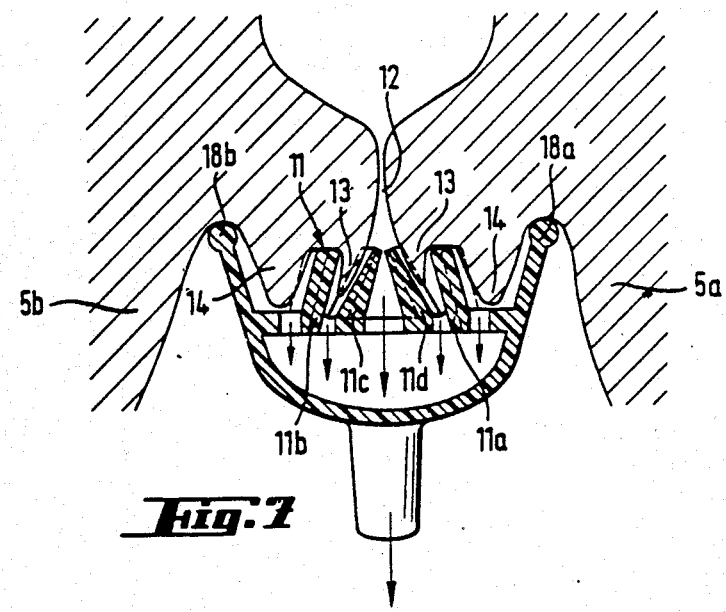
FIG. 7 is a cross sectional view of a second variant embodiment of an inventive urine collector, which collector is being worn.

In cases where the seal provided by the above-descirbed first embodiment of the inventive urine collector 1 appears to be placed in question as a result of anatomical idiosyncrasies or a high intensity of movement or the woman's frequent and extended assumption of reclining positions, a second variant embodiment according to FIG. 7 may be employed. The only difference between this and the first embodiment is that the variant according to FIG. 7 has a dual collector structure 11, comprising two pieces 11c and 11d disposed interiorly of and generally parallel to pieces 11a and 11b. These pieces 11c and 11d are worn between the labia minora 13, such that the urine exiting the urethra 12 is immediately captured by said pieces 11c and 11d.

Figure 8:
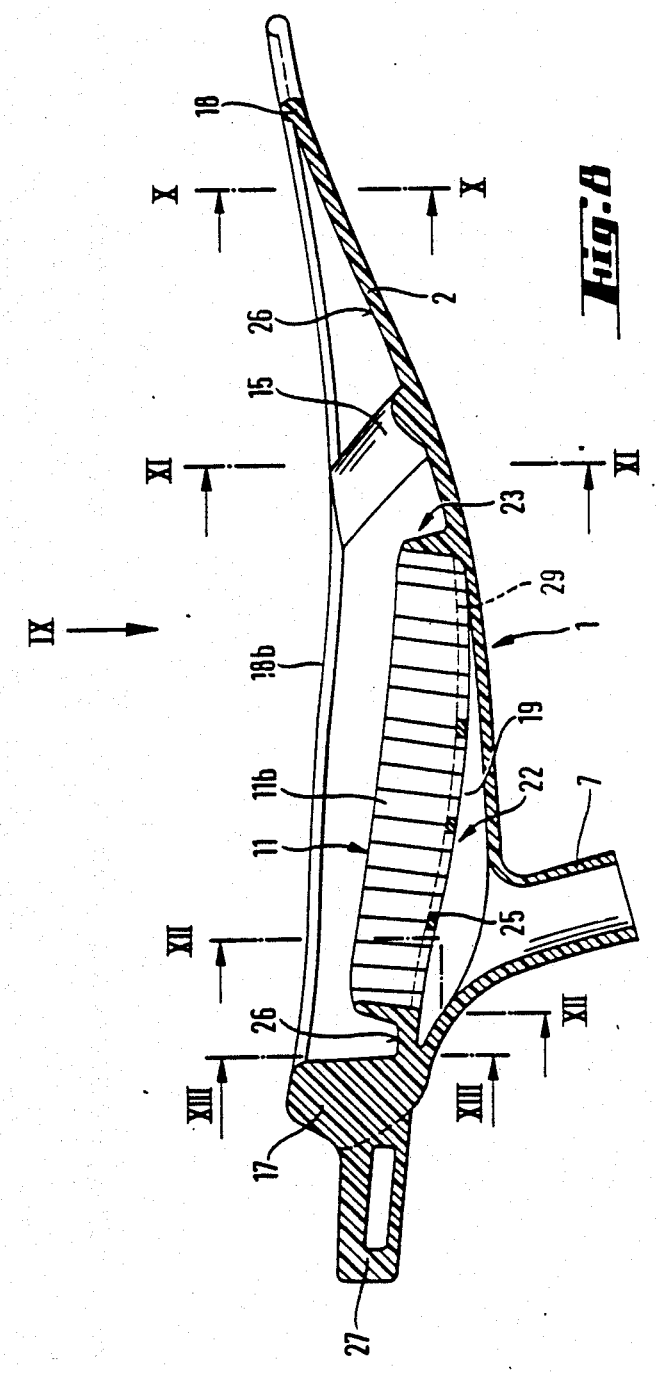
FIG. 8 is a longitudinal cross sectional view of a urine collector according to FIG. 6.

FIG. 8 is a longitudinal cross sectional view of an inventive urine collector 1 for women. The part 2 is shown, with its encircling border 18 as a sealing and reinforcing means, and with an elongated reinforcing member 26 (FIG. 9) disposed centrally and longitudinally in the forward region. The part 2 bears the collector structure 11 interiorly. The collecting cavity 19 extends below the structure 11, and the outlet 7 leads out of cavity 19. The front bead 15 which extends through the entire transverse extent of the part 2, which bead together with the lateral regions 18a and 18b of the border 18 and the rear bead 17 delimits the moist zone 23, can also be seen clearly. An extension 27 to which the auxiliary belt (4a, 4b) (not shown here) can be attached or through which said belt can be passed may be seen adjoining bead 17.

Figure 9:
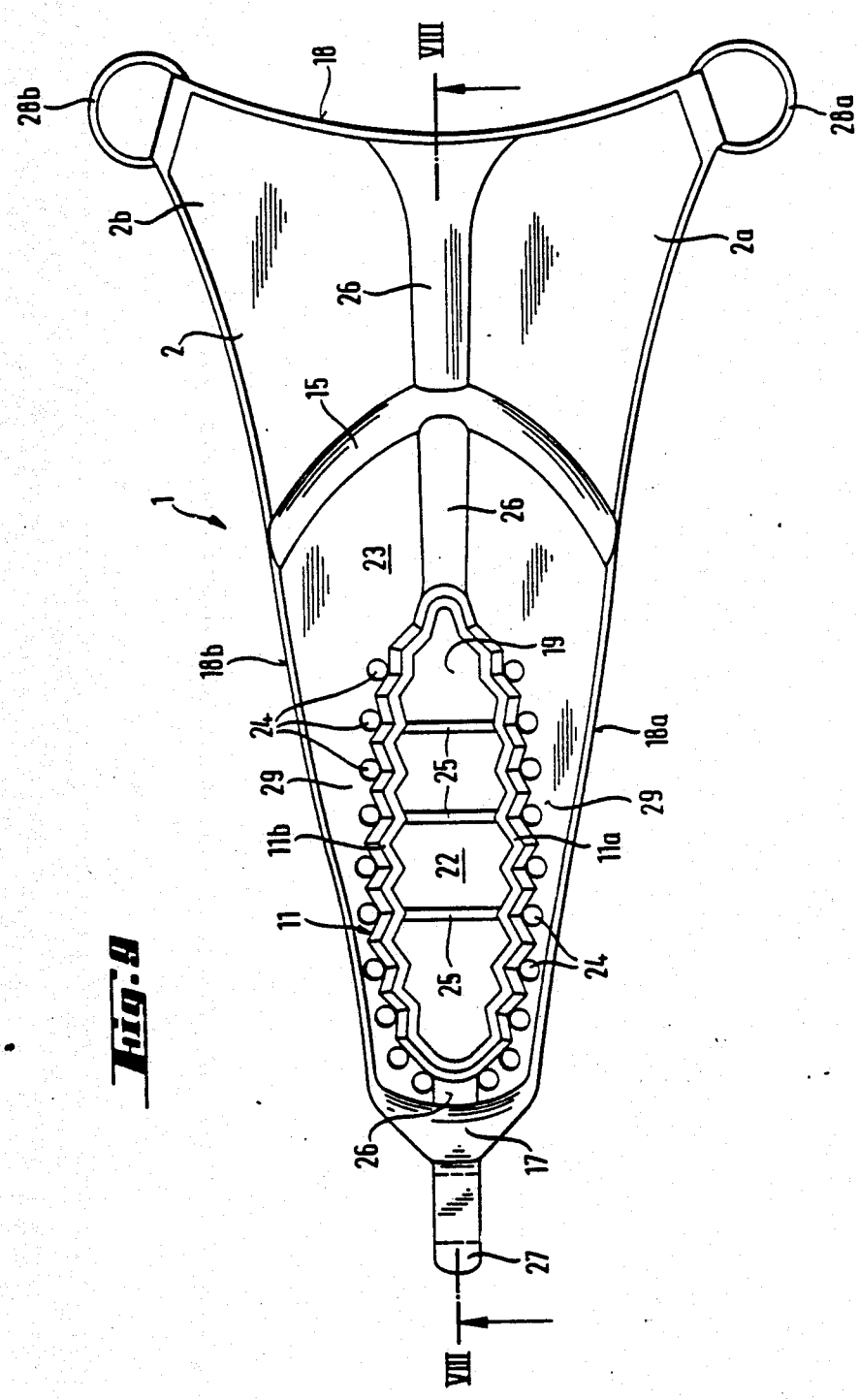
FIG. 9 is a plan view of the urine collector of FIG. 8, in the direction of arrow IX.

In FIG. 9 the urine collector 1 of FIG. 8 is shown from the direction of arrow IX. Here one can also see the part 2 the perimeter of which is reinforced by the border (18, 18a, 18b). The collector structure 11 comprised of the two lateral pieces 11a and 11b is disposed in the rear, narrower region of part 2. The collecting cavity 19 with the outlet 7 (not shown here) is disposed under the structure 11. The two lateral pieces 11a and 11b of the collector structure 11 are prevented from collapsing together by the spacing member 25. To the rear, the border 18 and the collector structure 11 merge into the rear bead 17 which comprises the rear seal of the urine collector 1 up to the extension 27. In the wider front region the front bead 15 extends transversely over the part 2 (which part 2 includes the longitudinally disposed elongated reinforcing member 26) from one lateral border region 18a to the other 18b. The front bead 15 forms a front seal of the moist zone 23. Rings 28a and 28b are disposed on the two front ends 2a and 2b, respectively, of the part 2, to which rings the waist belt 3 (FIG. 3) can be attached.

As can be seen particularly well in this Figure, the side pieces 11a and 11b of collector structure 11 are comprised of zigzag-shaped prominences which advantageously are inclined inward. This configuration is reminiscent of the surface of a cactus and serves the same purpose, namely to drawn any incident moisture into the apices of the V's, thence to flow downward. In the collector structure 11 this occurs both interiorly, where the urine can flow unimpeded from the bottom edge into the collecting cavity, and exteriorly, where any incident urine is also drawn into the apices of the V's where it is guided downward and thus does not collect in the moist zone. As a further aid to prevent urine from collecting in the moist zone 23, advantageously a drainage hole 24 is disposed in the connecting member 29, in each "V" formed by the side pieces 11a and 11b, so as to ensure free drainage of the urine there into the collecting cavity 19 disposed thereunder.

Advantageously, the part 2 is manufactured from readily flexible material, whereby when the urine collector is supported on the rings 28a and 28b and the extension 27 the tensile forces exerted by the belts 3 and 4 result in th part 2 assuming a shell-like shape. This results in improved snug fitting of the urine collector and thus in better sealing, particularly in the application regions 20 and 21. On grounds of comfort and hygiene, the inventive urine collector may be worn with a sterile gauze pad applied over the collector structure 11 without suffering loss of effectiveness.

Figure 10:
FIGS. 10 to 13 are cross sectional views of the urine collector according to FIG. 8, along lines X—X, XI—XI, XII—XII, and XIII—XIII, respectively.
Figure 11:
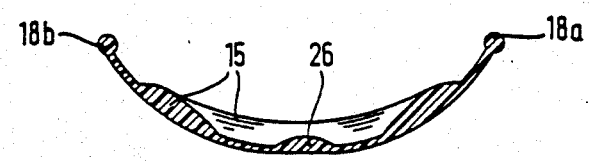
Figure 12:
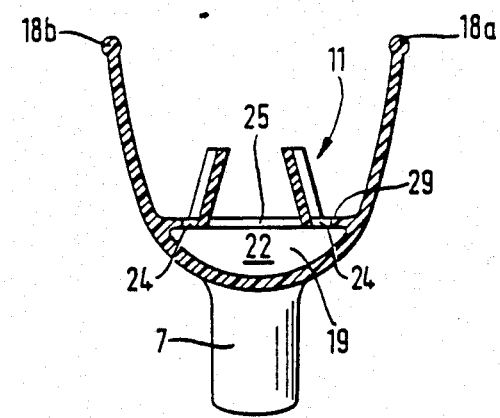
Figure 13:
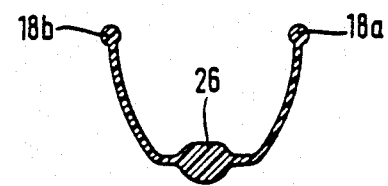

FIGS. 10 and 13 show cross sections through the urine collector according to FIGS. 8 and 9. These Figures do not require any special explanation.

FIGS. 14 to 23 illustrate a third variant embodiment of the inventive urine collector, wherein the part 2 has a slightly different shape than in the two abovementioned variant embodiments. In addition, the rear bead is provided with a marked prominence 17a in order to provide improved sealing against the region between the buttocks. Also, this embodiment does not have spacing members 25 between the side pieces 11 of the collector structure 11. The collector structure stands free over the collecting cavity 19 from which the outlet 7 leads. To increase wearing comfort, this embodiment comprises a pair of rings (28a, 28b) both in the front and the rear. As seen particularly from FIGS. 16 and 17, these rings are embedded in the part 2. It is recommended that the rear rings have a rectangular shape and the front rings a round shape (as shown in FIG. 15).

The longitudinal and transverse cross sectional views of this third variant embodiment shown in FIGS. 18 and 19 need no special explanation.

FIGS. 20, 21 and 22 are enlarged views of the region of the inventive urine collector interior to the dashed-line rectangle XX of FIG. 15. These Figures show clearly how the collector structure 11 and the rear bead 17 with prominence 17a cooperate. FIG. 20 also shows clearly how in this variant the drainage holes 24 are advantageously disposed around the perimeter of the collector structure 11.

FIG. 23 illustrates how the collecting cavity 19 can basically be comprised of a film joined to the part 2 at the lateral regions 18a and 18b of the border and at the beads 15 and 17.

FIGS. 24 to 26 illustrate a fourth variant embodiment of the inventive urine collector, wherein the side pieces 11a and 11b of the collector structure 11 are joined together at the top, in the locations of the inwardly directed V's. This enables dispensing with the spacing members 25 without incurring a risk that the collector structure 11 can be compressed together by external forces. This fourth variant embodiment further differs from the three others described supra in that the part 2 has a much smaller surface area and is much abbreviated in its rear. Also, the lateral regions 18a and 18b of the border 18 are provided with a sealing lip (which obviously also may be provided just as well in the other embodiments). Another difference in the fourth embodiment is that the drainage holes 24 may be trangular in shape, so as to match the "V" shape of the collector structure 11. If the part 2 bears a connecting eye or lug 30 on its front, the urine collector can be worn with a kind of suspenders arrangement instead of the waist belt 3 of FIG. 1. These suspenders comprises a band which rests between the breasts in front and splits into two bands running over the shoulders and the back to connect with the two rings 28a and 28b.

One skilled in the art can readily see that the inventive urine collector offers substantial advantages over all known apparatuses. It is of minimal size and it collects the uncontrolled urine excretions as close as possible to their exit point. The region of the female lower torso which is kept more or less moist over an extended period is limited practically to the labia miniora. This substantially prevents soreness and inordinate insult to the skin.

Obviously, the above-described urine colletor may be constructed differently in its details, if such differences are found advantageous. In particular, other means of connection with the bands or belts may be provided. Also, part 2 may have a different shape which may be otherwise adapted to anatomical parameters. The extent of the collector structure and the size of the part 2 obviously should be adjusted to fit so that a urine collector for a young, slender woman will look different from one for an old, corpulent woman.

Women who are confined to a wheelchair or who must sit for long periods may advantageously employ a horseshoe-shaped cushion which is open in front to facilitate the flow of urine out of the collector.

Obviously, the various variant embodiments of the inventive urine collector may be combined, so that other combinations of structural details may be employed which are not enumerated here.

I claim:

1. A urine collector for incontinent women comprising a crotch piece having a substantially longitudinal axis and provided with attachment points at each corner for support belts and an outlet for connection to a urine collecting bag; characterized in that a collector structure is disposed in the crotch piece with a collecting cavity disposed under said collector structure and said outlet leading out of said cavity, wherein said collector structure comprises two side walls having a zig-zag shape in plan view extending along the longitudinal axis of said collector and joining at the respective ends of said collector structure, the urine collector further characterized in having boundary means as part of the crotch piece defining a moist zone surrounding the collector structure beyond which boundary means urine cannot penetrate said boundary means comprising a border of said crotch piece and undergoing transition to front and rear beads inwardly of the front and rear edges of said crotch piece.

2. A urine collector according to claim 1 characterized in that the side pieces of the collector structure are connected on their exterior sides to the crotch piece and drainage holes are disposed at the bottom of each "V" formed by the zigzag configuration through which urine can flow into the collecting cavity.

3. A urine collector according to claim 1 characterized in that the collector structure further comprises two additional side pieces of zigzag cross section disposed inwardly of and generally parallel to the first side pieces.

4. A urine collector for incontinent women comprising a crotch piece of substantially triangular shape, the apex being located perineally, having suspensory means attached thereto and an outlet therefrom attached to a urine collection bag, said crotch piece comprising a collector structure arranged above a collecting cavity from which cavity said outlet extends, and boundary means, said collector structure being within said boundary means and defining a wet zone, said boundary means comprising the lateral edges of said crotch piece transversely connected by forward and rearward beads, said forward transverse bead being located between said collector structure and the base of said triangular shape which together define a moist zone, said collector structure comprising side pieces of zig-zag configuration extending along a longitudinal axis of said collector and connected at the ends to form a wall surrounding said wet zone and having spacing members extending between said side pieces to maintain their separation under outside forces.

5. A urine collector as in claim 4 wherein said suspensory means comprise a waist belt and an auxiliary belt, attached to the crotch piece at its corners, said auxiliary belt passing through the apex with its ends being attached to said waist belt.

6. A urine collector as in claim 4 wherein said collector structure comprises first and second pairs of zigzag side pieces, each pair connected at their ends, and said first pair located outwardly of said second pair thereby defining a space therebetween for receipt of a wearer's labia minora.

7. A urine collector as in claim 4 wherein said crotch piece further comprises a longitudinally extending elongated reinforcing member extending forward of said collector structure to the base of said triangular shape.

8. A urine collector as in claim 4 having drainage holes located at the base of said collector structure at the bottom of each "V" formed by the zigzag configuration of said structure.

9. A urine collector as in claim 6 wherein said collector structure further comprises drainage means in the space between said first and second pairs of zigzag side pieces.

* * * * *